United States Patent
Deck et al.

(10) Patent No.: US 6,661,509 B2
(45) Date of Patent: Dec. 9, 2003

(54) METHOD AND APPARATUS FOR ALIGNMENT OF MULTIPLE BEAM PATHS IN SPECTROSCOPY

(75) Inventors: Francis J. Deck, Madison, WI (US); Richard C. Wieboldt, Verona, WI (US)

(73) Assignee: Thermo Electron Scientific Instruments Corporation, Madison, WI (US)

( * ) Notice: Subject to any disclaimer, the term of this patent is extended or adjusted under 35 U.S.C. 154(b) by 152 days.

(21) Appl. No.: 09/778,485

(22) Filed: Feb. 7, 2001

(65) Prior Publication Data

US 2002/0105640 A1 Aug. 8, 2002

(51) Int. Cl.$^7$ .................................................. G01J 3/44
(52) U.S. Cl. ........................................ 356/301; 356/399
(58) Field of Search ................................ 356/301, 399, 356/302, 309, 326, 338

(56) References Cited

U.S. PATENT DOCUMENTS

| | | | |
|---|---|---|---|
| 3,782,823 A | 1/1974 | Kantorskj et al. | |
| 4,218,112 A | 8/1980 | Ruker | |
| 4,523,799 A | 6/1985 | Delhaye et al. | |
| 5,596,404 A | 1/1997 | Beck et al. | |
| 5,614,726 A | 3/1997 | Kaye et al. | |
| 5,623,342 A | * 4/1997 | Baldwin et al. | 356/301 |
| 5,703,683 A | 12/1997 | Hunt et al. | |
| 5,745,308 A | 4/1998 | Spangenberg | |
| 5,818,579 A | 10/1998 | Beck et al. | |
| 5,822,061 A | 10/1998 | Delhaye et al. | |
| 5,912,734 A | 6/1999 | Beck et al. | |
| 5,917,971 A | * 6/1999 | Slater | 385/31 |
| 5,999,255 A | 12/1999 | Dupee et al. | |
| 6,067,154 A | * 5/2000 | Hossain et al. | 356/237.2 |
| 6,108,081 A | * 8/2000 | Holtom et al. | 356/301 |
| 6,128,077 A | * 10/2000 | Jovin et al. | 356/310 |

OTHER PUBLICATIONS

Lars Markwort, et al. "Raman Imaging of Heterogeneous Polymers: A Comparison of Global versus Point Illumination," Applied Spectroscopy, vol. 49, No. 10, 1995, pp. 1411–1430.

* cited by examiner

*Primary Examiner*—Daniel St. Cyr
(74) *Attorney, Agent, or Firm*—Foley & Lardner (57) ABSTRACT

Alignment of multiple beam paths in a microscope such as a Raman spectrographic microscope utilizes an alignment instrument that is mounted on the stage of the microscope and positioned by the operator until an aperture of the alignment instrument is at an intended focal point of the microscope. A light source within the alignment instrument is turned on to project light through the aperture which is passed on a return light beam path to the input aperture of a spectrograph where it is detected. Features are included in the return beam path to adjust the beam path until the light detected is maximized, thereby aligning the return beam path to the intended focal point. The light source in the alignment instrument is turned off and a light source in the microscope system, such as a laser, is activated to provide an illumination light beam on a beam path that extends through the objective lens of the microscope, which focuses the beam onto the alignment instrument. The illumination beam that passes through the aperture is detected by a detector within the alignment instrument. The illumination beam path is then adjusted until the detected light is maximized, thereby aligning the illumination beam path to the intended focal point.

14 Claims, 5 Drawing Sheets

METHOD AND APPARATUS FOR ALIGNMENT OF MULTIPLE BEAM PATHS IN SPECTROSCOPY

FIELD OF THE INVENTION

This invention pertains generally to the field of microscopic spectroscopy such as Raman spectroscopy.

BACKGROUND OF THE INVENTION

When illuminating light, such as a laser beam, is incident upon a sample material, molecular bonds in the material will be excited by the incident light and will emit radiation which can be detected as scattered light. The Raleigh component of the scattered light corresponds to the light emitted when the molecule relaxes from the excited state to the ground state. Infrequently, the molecule will relax to a different vibrational or rotational level in the ground state. This produces Raman scattering components at Stokes and Anti-Stokes frequencies. A sample composed of multiple molecular species will produce a spectrum of such Raman scattering. The Raman scattering components can be detected and analyzed to help determine the composition of the sample. Various apparatus have been developed for analyzing Raman spectra including Raman microscopes in which a very small area on a sample can be analyzed to determine characteristics of the composition of the sample at that area. In a typical Raman microscope, narrow band or monochromatic illuminating light, such as from a laser, is passed along a beam path through the objective lens of the microscope where it is focussed at a focal point on a specimen. The Raman scattering from the sample collected by the microscope objective is passed back on a beam path to a spectrograph which typically separates the Raman scattering radiation by wavelength and detects it. Optical elements are typically included in the excitation beam path and the returning Raman radiation beam path to separate the excitation light from the Raman scattering light and to filter out the Raleigh light from the beam directed to the spectrograph. The microscope may also include a wide field illumination beam path in which light from the microscope is passed up on a beam path to a position where it can be viewed directly by an operator or detected by a video camera for display to an operator.

In using a Raman microscope of this type, the operator will generally view the specimen through the microscope to select a small area in the specimen to be analyzed, generally by aligning the desired area to be analyzed in the center of the microscope visual field, typically with the aid of cross hairs or other indicia. The intention is that the illuminating light beam path will have its axis aligned with the visual beam path so that the illuminating light will be focussed onto the spot in the specimen that was targeted by the operator using the microscope. However, if the illuminating light beam is not, in fact, aligned with the axis of the visual microscope beam path, the illuminating light will impinge on the sample at a different position, leading to potentially erroneous data concerning the composition of the sample. In addition, if the returning beam path which includes the Raman scattering radiation is not properly aligned with the aperture of the spectrograph, the intensity of the (already very weak) Raman scattering radiation received by the spectrograph will be reduced. This loss of signal power can give rise to corruption of the spectrographic data by noise and a reduction of the full potential of the spectroscopic microscope to obtain information concerning the composition of the sample.

All Raman microscope systems are subject to minor alignment drift over time. These drifts can be caused, for example, by environmental changes due to temperature fluctuations and external vibration, and by normal wear of components occurring during operation. Over time, the performance of the Raman microscope system degrades and the misalignments must be corrected by periodic maintenance procedures. Such maintenance is frequently difficult because of the complexity of simultaneously aligning the various beam paths, and generally requires trained maintenance personnel. This maintenance is thus costly both because of the direct expense associated with the maintenance procedures and because of the down time of the microscope during the maintenance procedures.

SUMMARY OF THE INVENTION

In accordance with the present invention, alignment of the multiple beam paths in a spectrographic microscope such as a Raman microscope is carried out rapidly and efficiently, without the need for trained maintenance personnel, and with minimal operator involvement. The alignment procedure may be carried out under software control by the microscope system computer. Because the alignment process is quickly and easily carried out, realignment can be performed much more frequently with minimal instrument down time, allowing the instrument to be maintained at peak performance levels.

In carrying out the invention, the operator of the microscope uses the visual microscope to position an aperture at an intended focal point of the microscope. This aperture can comprise an entrance aperture for a detector, an exit aperture for a source, or both. After the operator has fixed the aperture at the intended focal point, the spectroscopic microscope system may then be operated to either detect light using the spectrographic detector that exits from the aperture or to project illuminating light through the microscope to be focussed at the aperture and detected. The illuminating light beam path may then be adjusted to maximize the intensity of the light passed through the aperture and detected, and the return beam path leading to the spectrograph may be adjusted to maximize the light exiting from the aperture that is detected by the spectrograph. The maximization of the detected light in the illuminating beam path ensures that the illuminating beam is maximally aligned to focus on the intended focal point, whereas maximization of the detected light in the return beam path will result in the maximum return of Raman scattered light from a specimen that emanates from the focal point of a sample mounted on the microscope.

An alignment instrument that may be utilized in accordance with the invention comprises a housing having a plate with a spatially limited aperture therein, e.g., a pinhole aperture. A light source is mounted within the housing and is selectively activatable to project light out of the housing through the aperture. A light detector is also mounted in the housing to detect light originating outside the housing that passes through the aperture. The detector provides an output signal which corresponds to the intensity of the detected light. The alignment instrument is preferably formed so that it is readily mountable on the stage of the microscope, which can be adjusted until the operator, using the visual system of the microscope, observes the aperture of the alignment instrument located at the desired focal point of the microscope objective lens. Indicia may be provided in the microscope in a conventional manner to help locate the focal point. The alignment instrument may then be used without moving it from that position to project light out from the aperture to be detected by the spectrograph detector for maximization of the return beam path and, separately, to detect light from the illuminating beam that is focussed onto the focal point and passed through the aperture to allow adjustment of the illuminating beam to properly align it.

In the present invention, means are preferably provided in the illumination beam path to adjust the axis of the beam to allow it to be aligned to the aperture of the alignment instrument. Similarly, adjustment means are preferably provided in the return beam path to allow adjustment of the axis of the return beam to best fit the return beam to the input aperture of the spectrograph. A preferred structure for such adjustment means includes a pair of sequential lenses in the beam path which are adjustable relative to one another in two dimensions. Preferably, the pair of lenses have focal lengths of equal magnitude but opposite sign. One lens may be fixed and simply compensates for the other to produce a system with negligible optical power. The adjustable lens can be displaced from the optical axis in two dimensions, so that the pair of lenses can be used to effectively introduce an angular deviation to the beam passing through it. The motion of the adjustable lens may be controlled by motor drives in the two dimensions.

The alignment process in accordance with the invention may be carried out automatically under computer control. The microscope system may be programmed to periodically prompt the operator to perform alignment or it may provide a prompt when the need for realignment is detected. The operator places the alignment instrument on the stage of the microscope and adjusts the centration and focussing of the microscope using the oculars or a video display to position the aperture of the alignment instrument at the desired focal point of the microscope. This alignment procedure defines the microscope axis. After this procedure has been performed by the operator, the operator enables the system to carry on the alignment process automatically. The system turns on the alignment instrument light source and adjusts the spectrograph beam path, utilizing the adjustment means, to maximize the intensity of radiation entering the spectrograph. The system then turns off the light source in the instrument, and turns on the illuminating light source in the microscope, typically a laser. The system then adjusts the illumination beam path using the illumination beam adjustment means to maximize the intensity of radiation passing through the aperture of the alignment instrument and that is detected by the detector within the instrument. After these processes are completed, the system then can provide a message to the operator that alignment has been completed and that the alignment instrument may be removed from the microscope stage.

Further objects, features and advantages of the invention will be apparent from the following detailed description when taken in conjunction with the accompanying drawings.

DETAILED DESCRIPTION OF THE INVENTION

Figure 1:
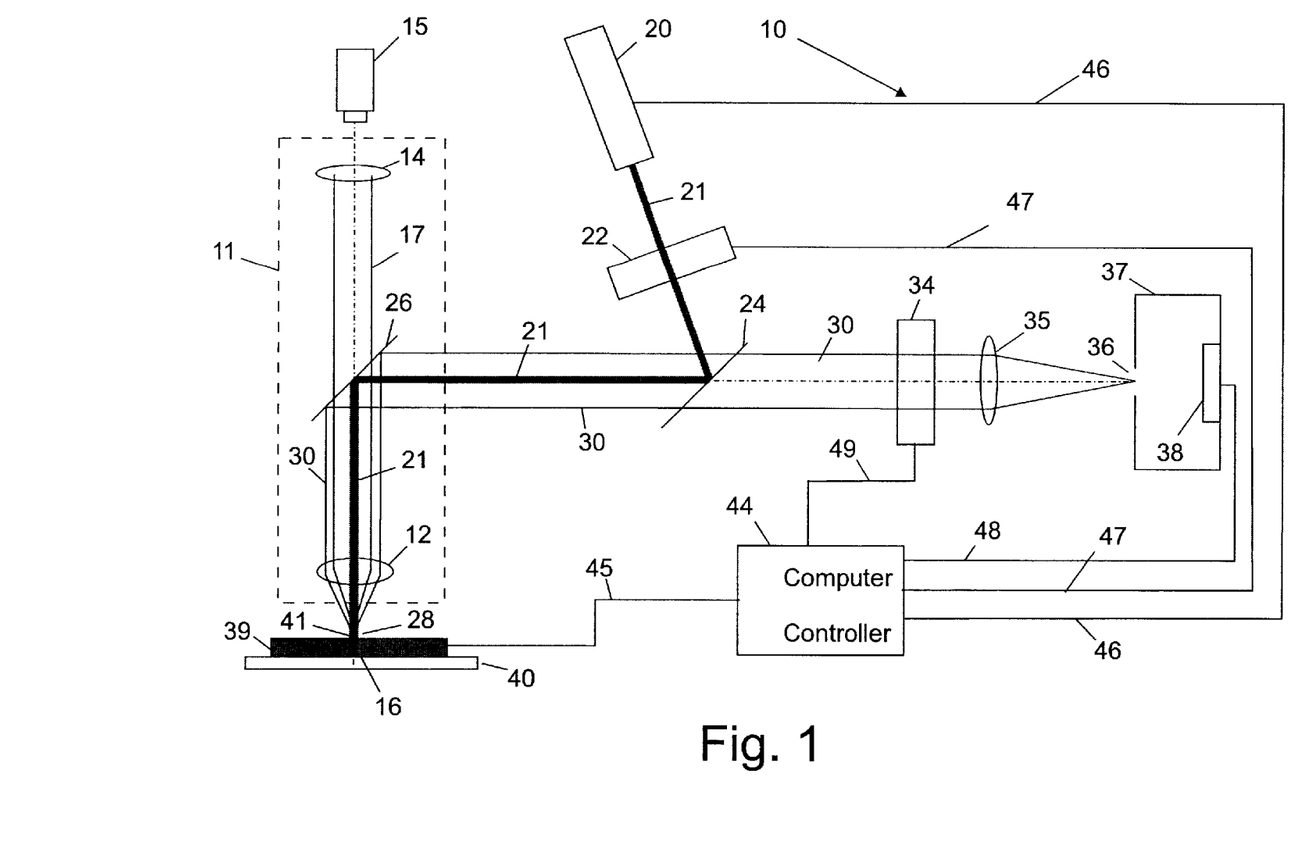
FIG. 1 is a schematic diagram of a Raman spectrographic microscope system in accordance with the invention.

With reference to the drawings, a spectroscopic microscope system is shown generally at 10 in FIG. 1. The system 10 is suited for Raman spectroscopy, but the invention may be used with other types of optical systems having similar multiple beam paths, for example, confocal fluorescence microscopes. The microscope system 10 includes an optical microscope shown in simplified form within the dashed lines labeled 11 in FIG. 1. The microscope 11 includes an objective lens 12 and an ocular lens or lenses 14 which may be utilized for direct viewing by an observer or which may form part of or be in addition to the lenses within a video camera 15. Light from a sample located at a sample position 16 is thus passed back through the objective lens 12 to the ocular lenses 14 on a beam path 17 in a conventional fashion to form an image that can be viewed by the operator either directly or with the use of the video camera 15 and a video display terminal.

In the microscope system of FIG. 1 for use in Raman spectroscopy, illuminating light is provided from a source 20, typically a laser, on an illuminating beam path 21 through a beam path adjustment unit 22 to a deflecting mirror and notch filter 24 which redirects the illuminating beam 21 on a path toward a Raman interface module deflecting mirror 26. The deflecting mirror 26 may be formed as a plane mirror or as a dichroic mirror mounted on a motorized slide for selectable insertion into and removal out of the microscope optical beam path 17. When the deflecting mirror 26 is moved into position in the beam path 17, it deflects the illuminating beam 21 onto a beam path which is collinear with the microscope optical beam path 17. The objective lens 12 focuses the illuminating beam onto a focal point 28.

The microscope system also includes a Raman return beam path 30 which is comprised of the scattered light that is collected by the objective lens 12 and formed into a collimated beam which is deflected by the deflecting mirror 26 onto a path collinear with the illuminating beam path 21 up to the position of the notch filter 24. The notch filter 24 is formed to transmit the wavelengths of the Raman radiation in the beam 30 and to reflect the wavelengths of the illuminating beam 21 and of the Rayleigh radiation. The notch filter may be a holographic filter and is used for Rayleigh rejection in the manner described in F. J. Bergin, Spectrochemica Acta, Vol. 46A, No. 2, 1990, pp. 153–159. After passing through the notch filter 24, the Raman radiation on the beam path 30 passes through a beam, path adjustment mechanism 34 and through an input lens 35 which focuses the beam 30 onto the aperture 36 of a spectrograph 37. The spectrograph 37 may be formed to spatially distribute the wavelengths of light in the beam 30 which are then incident upon a detector 38 which detects the intensity of the light at the various wavelengths to provide an output signal indicative of the Raman spectrum for a sample.

In accordance with the invention, when the microscope system 10 is carrying out alignment, an alignment instrument 39 in accordance with the invention is mounted on the stage 40 of the microscope. As explained further below, the alignment instrument 39 includes a spatially limited aperture 41 which is positioned by the operator to coincide with the central axis of the microscope optical beam 17. A computer controller 44 provides control signals to and receives signals from the alignment instrument 39 on lines 45. In addition, the computer controller is connected to the laser or other source 20 by a control line 46, to the beam adjust mechanism 22 by a line 47, to the detector 38 by a line 48, and to the beam adjust mechanism 34 by a line 49. As discussed further below, the computer controller can carry out automatic alignment adjustments utilizing the adjustment mechanisms 22 and 34 under software control once the operator has positioned the alignment device 39 so that the aperture 41 is aligned with the focal point of the microscope.

Figure 2:
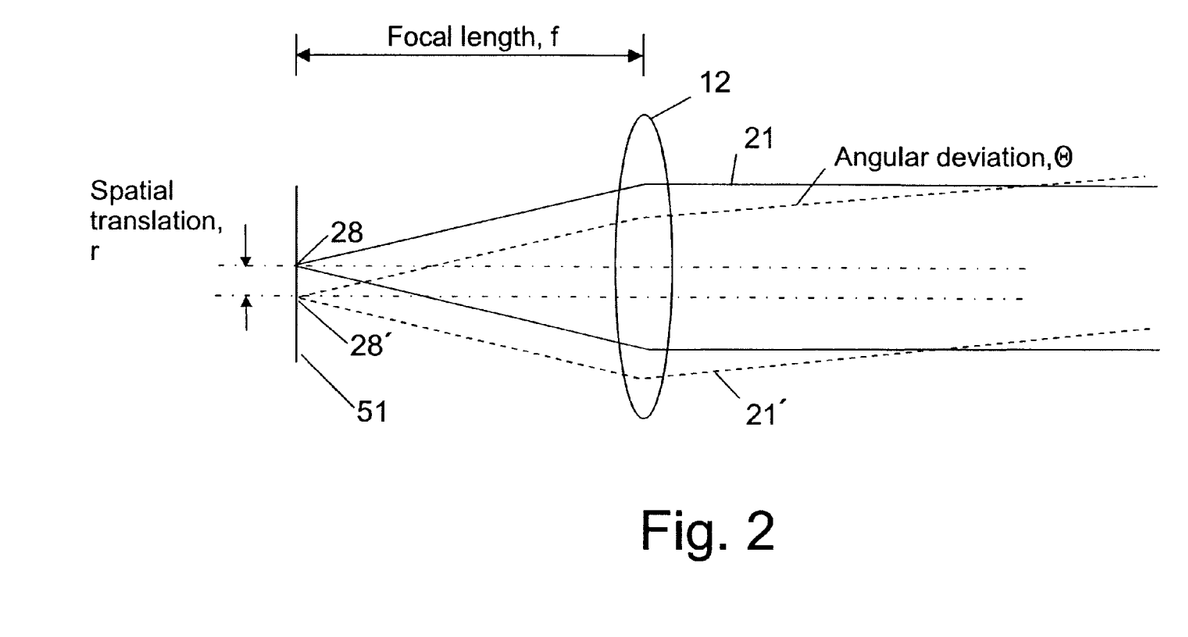
FIG. 2 is a diagram illustrating the effects of misalignment of the beam path in the microscope system.

The effects of misalignments of the beams within the microscope is illustrated in FIG. 2, which shows the illuminating beam 21 passed through the objective lens 12 and focused to the focal point 28 lying in a focal plane 51 of the microscope. Angular deviations in the collimated beam 21 are transformed into spatial translations r at the focal plane in accordance with:

$r = f\theta$

Where r=spatial translation away from the center of the optical axis, f=focal length of the lens, and $\theta$=the angular deviation of the beam.

For example, the focal length of a 100× objective is 1.6 mm, a 50× is 3.2 mm, and a 20× is 8 mm. A typical focal length for the spectrograph input is 40 mm.

A signal can be obtained without alignment of the microscope beam path 17 at the expense of allowing visual observation of the Raman sampling point 28, but this would sacrifice a major feature of the optical microscope system. The optical microscope beam path 17 is typically not provided with any alignment adjustment. Thus, in the present invention, the illumination beam path and the return beam path to the spectrograph are adjusted to allow for independent angularity adjustments of these beam paths with respect to the focal point that has been determined by the microscope beam path 17.

Figure 3:
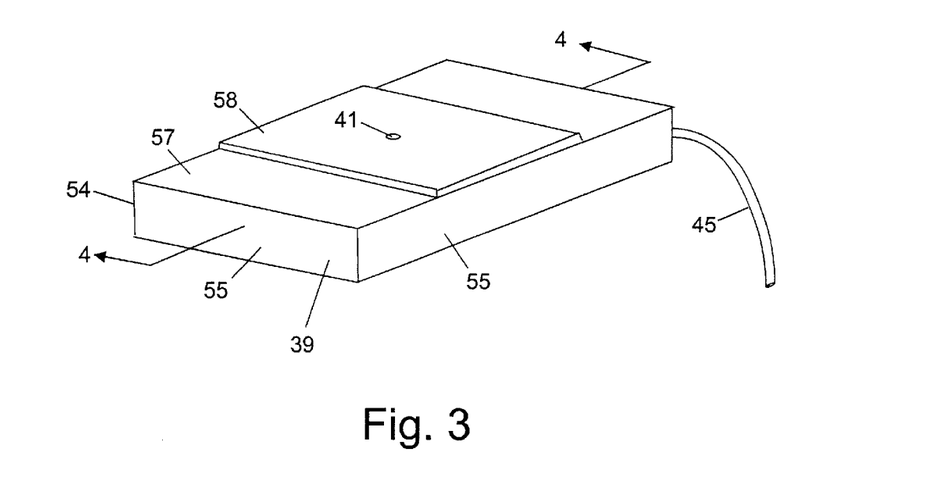
FIG. 3 is a perspective view of an alignment instrument in accordance with the invention.

As illustrated in FIG. 3, the alignment instrument 39 includes a housing 54 formed of sidewalls 55, a bottom wall 56 and a top wall 57 which may form or which may have mounted thereon a face plate 58. The face plate 58 has the aperture 41 formed therein, as best illustrated in the cross-sectional view of FIG. 4. The aperture 41 acts as both an exit aperture for light exiting from the alignment instrument and as an entrance aperture for light entering the alignment instrument. The aperture 41 is spatially limited and preferably is formed as a pinhole aperture. In a confocal microscope, there is a magnification factor from the sample focal plane to the confocal aperture. The aperture diameter should be such that, when magnified by this factor, the resulting image at the confocal aperture is roughly matched to the diameter of the confocal aperture. For example, for a confocal aperture diameter of 25 µm and a magnification factor of 2.5, a preferred pinhole aperture diameter is 10 µm. Generally, a relatively broad range of pinhole aperture diameters is feasible. The pinhole preferably is not significantly smaller than the ideal diameter, since such a pinhole would have some latitude to move around while the image remains fully enclosed within the diameter of the confocal aperture. The aperture diameter should also roughly match the diameter of the laser focal spot.

Figure 4:
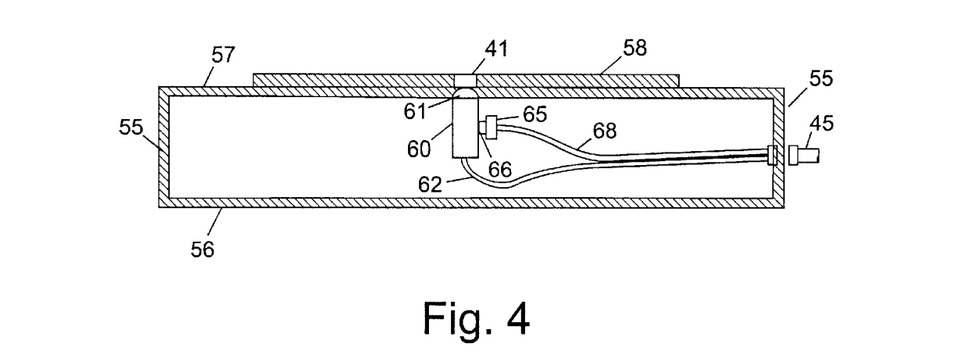
FIG. 4 is a cross-sectional view of the alignment instrument taken generally along the lines 4—4 of FIG. 3.

As shown in FIG. 4, a light source 60, such as a high intensity light emitting diode (LED), may be mounted within the housing. An example is a Chicago Miniature T-1 ⅔ Ultra Bright LED which nominally emits at 635 nm. An emission wavelength is preferred that is in almost the middle of the spectral range over which the instrument is used to reduce any possible chromatic aberration effects. The LED source 60 preferably includes a lens 61, integrated into the LED casing 66, that is positioned under the pinhole aperture 41. When the source 60 is provided with power on a line 62 which extends back on the line 45 to the computer controller, the light from the source is directed by the lens 61 to exit the aperture 41 to provide essentially a "point-source" of light. For detection of light passing into the aperture 41, a detector 65 is mounted to the casing 66 of the LED source to detect the light that passes through the aperture 41 and the lens 61 into the center of the casing and is diffused by the interior walls of the (e.g., clear plastic) casing such that some of the light is incident on the detector 65. The detector 65 (e.g., a silicon photodiode such as the VTB-100 from EG&G) puts out an output signal proportional to the detected light intensity on a line 68 which forms part of the line 45 that extends back to the computer controller. It is understood that other means may be utilized to couple both a light source and a detector to the aperture 41. For example, the source 60 and the detector 65 may be mounted to a slide mechanism to be separately indexed into and out of position under the aperture 41, or may be coupled to the aperture through a dichroic mirror, a beam splitter, optical fiber couplers, etc. Other light sources such as lamps, etc. and other detectors may be used.

Figure 5:
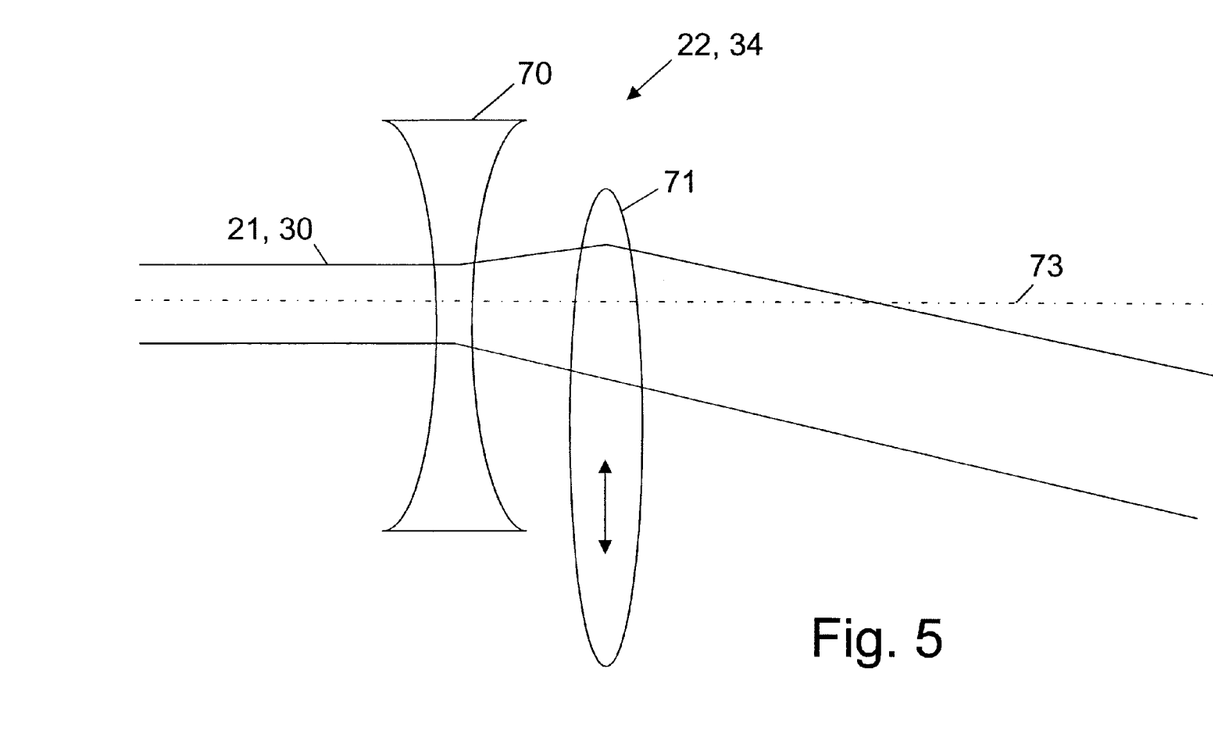
FIG. 5 is an illustrative view of a pair of lenses that may be utilized to provide two-dimensional adjustment of the beams in the microscope system.
Figure 6:
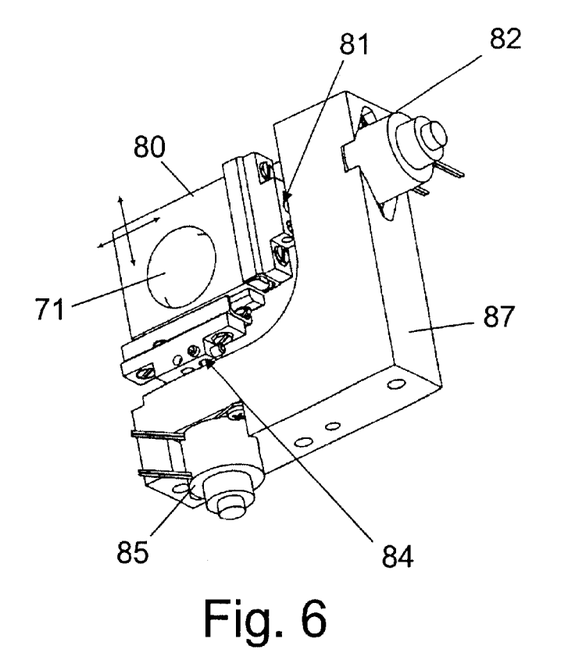
FIG. 6 is a front perspective view of a beam adjustment mechanism that may be used in the invention.
Figure 7:
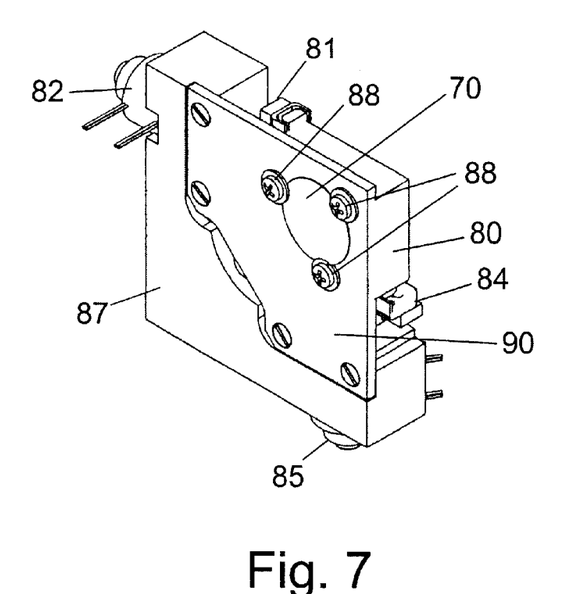
FIG. 7 is a back perspective view of the beam adjustment mechanism of FIG. 6.

A preferred arrangement for the beam adjustment mechanisms 22 and 34 for adjusting the beams 21 and 30 is shown schematically in FIG. 5. The exemplary beam adjustment mechanism comprises a pair of lenses 70 and 71 which are mounted sequentially (in the beam path 21 or 30). One of the lenses 70 or 71 (e.g., lens 71 as shown in FIG. 5) is mounted for translation in two dimensions in a plane perpendicular to the axis 73 of the incoming beam 21 or 30. For example, as shown in FIG. 6, the lens 71 may be mounted on a holder 80 connected to a slide 81 (e.g., a ball bearing slide) which is driven by a motor 82 (e.g., a stepper motor) in translation along an X axis, with the holder 80 mounted to another slide 84 which is driven by a stepper motor 85 in a Y axis direction. The stepper motors 82 and 85 are mounted to a base 87. As shown in the back side view of FIG. 7, the fixed lens 70 is mounted by locating pins 88 to a plate 90 which is mounted to the base 87. Both motors may be supplied with power from the computer controller 44 to drive the lens 71 to a desired position. The two stepper motors are preferably operated independently (not at the same time) so that new measurements can be made at each step in a raster pattern. The lenses 70 and 71 preferably have focal lengths of equal magnitude but opposite sign. The lenses compensate one another and the combination has negligible optical power. By displacing the lens 71 from the optical axis, an angular deviation is provided to the beam passing through it. Such a mechanism allows significant mechanical advantage, allowing the use of a motor drive that has relatively coarse mechanical resolution.

In carrying out alignment in accordance with the invention, the operator places the alignment instrument 39 on the stage 40 of the microscope and adjusts the microscope until the aperture 41 is at the intended focal point target position as seen by the operator through the ocular lenses 14 or as displayed in a video screen connected to the video camera 15. The computer controller 44 is then enabled by the operator to begin the alignment process. The controller turns on the alignment instrument light source 60 and then utilizes the adjustment mechanism 34 to adjust the Raman return beam path to maximize the intensity of the radiation entering the spectrograph and detected by the detector 38. Various optimization techniques may be utilized to carry this out. An example algorithm is a "grid search" followed by simplex maximization. This may be carried out, for example, utilizing the Nicolet OMNIC™ software (Thermo Nicolet Corporation). The alignment of the two beam paths (laser and spectrograph) use essentially the same software procedure:

The software measures a signal intensity on a "grid" of points, covering the range of travel in two axes of the motorized adjustment devices 22 and 34. The grid spacing is kept small enough to ensure that a significant signal level will be detected in at least one position.

The position on the grid where the strongest signal was observed is chosen as the starting point for the simplex optimization algorithm.

A simplex optimization algorithm fine-tunes the motorized adjustment devices to maximize the signal.

For the laser beam path, the laser is the light source and the "signal" is the photocurrent in the detector located in the alignment instrument 39. The motorized adjustment mechanism 22 in the laser beam path is used to maximize this signal.

For the spectrograph beam path, the source 60 in the alignment instrument 39 is the light source, and the "signal" is the intensity of radiation reaching the detector 38 inside the spectrograph. The motorized alignment mechanism 34 in the spectrograph beam path is used to maximize this signal.

After the beam path to the spectrograph has been optimized, the computer controller 44 then turns off the light source 60, turns on the laser 20, and adjusts the illuminating beam path 21 utilizing the beam path adjustment mechanism 22 to maximize the illuminating light passing through the aperture 41 and detected by the detector 65. Again, the computer controller utilizes a maximization technique, such as the simplex method, to find the maximum light intensity from the detector. After the adjustments have been carried out to maximize the beam path for the illuminating beam, the laser is turned off, and the computer controller may prompt the operator to remove the alignment instrument 39 from the microscope stage 40 so that the microscope system may be used for analyzing samples. The alignment instrument 39 is preferably conveniently mounted to the microscope system for ready access by the operator when another alignment procedure is to take place. The simple mounting of the alignment instrument 39 onto the microscope stage 40 and the location of the aperture 41 of the alignment instrument at the focal point using the optical microscope is a simple procedure that may be carried out by the operator of the microscope system without special training. Thus, alignments can be carried out at any time, and preferably on a periodic basis to maintain the microscope system at peak performance.

It is understood that the invention is not confined to the particular embodiments set forth herein as illustrative, but embraces all such modified forms thereof as come within the scope of the following claims.

What is claimed is:

1. A method for aligning beam paths in a microscope system having an illumination light beam path from a source to an objective lens of the microscope, the illumination light beam being focussed by the objective lens at a focal point in a sample position at which a sample may be located, a scattering light return beam path for scattering light collected from the sample position by the objective lens that extends to a light detector, and a visible light microscope beam path from the sample position through the objective lens to form an image of the sample position which may be observed by a viewer directly or with use of a video camera, comprising the steps of:

(a) positioning a spatially limited entrance aperture in the sample position at an intended focal point of the objective lens;

(b) passing illuminating light from the source on the illuminating beam path through the objective lens toward the entrance aperture positioned at the intended focal point and detecting the light passed through the entrance aperture, and adjusting the illumination beam path until the detected light is maximized;

(c) positioning a spatially limited exit aperture in the sample position at the intended focal point of the objective lens; and (d) projecting light through the exit aperture located at the intended focal point into the objective lens and passing the light on the return beam path to the light detector and detecting the light by the detector, and adjusting the return beam path until the output of the light detector is maximized.

2. The method of claim 1, wherein the entrance aperture and the exit aperture are the same aperture.

3. The method of claim 2, wherein the steps of positioning the aperture comprising the exit and entrance aperture comprises observing the image of the aperture provided on the optical beam path of the microscope and adjusting the position of the aperture until it is at the intended focal point of the objective lens of the microscope.

4. The method of claim 3, wherein the aperture is formed in a face plate of a housing of an alignment instrument that includes a light source mounted in the housing for projecting light through the aperture out of the housing and a detector for detecting light passed through the aperture into the housing, and including the step of mounting the alignment instrument on a stage of the microscope in position to allow the image of the aperture in the face plate to be viewed in the image from the optical beam path of the microscope.

5. The method of claim 3, wherein, after the step of positioning the aperture at the intended focal point of the objective lens, further including the steps of inserting a deflecting mirror in the microscope optical beam path and deflecting the illuminating light beam from the source to the objective lens using the deflecting mirror, and deflecting the Raman light collected by the objective lens by the deflecting mirror on a return beam path to the Raman light detector.

6. The method of claim 1, wherein the steps of adjusting the illumination beam path and the return beam path are carried out in each beam path with a pair of sequential lenses with focal lengths of equal magnitude but opposite sign, one of the lenses being translatable in two dimensions away from the central optical axis, by adjusting the position of the movable lens in each pair in each beam path to adjust the beam path.

7. A Raman spectrographic microscope system comprising:

(a) optical elements including an objective lens defining a microscope optical beam path for light from a sample position at which a sample may be located collected by the objective lens that extends to an image position at which an image of the sample position may be observed;

(b) optical elements defining an illuminating beam path from an illuminating light source to the objective lens, the objective lens focusing the illuminating beam to a focal point in the sample position;

(c) a spectrograph including an input aperture and a detector for detecting light entering the input aperture o#the spectrograph;

(d) optical elements including the objective lens defining a Raman scattered light return beam path from the objective lens to the input aperture of the spectrograph;

(e) means interposed in the illumination beam path for selectively displacing the illumination beam from an axis of the beam;

(f) means interposed in the Raman scattered light return beam path for displacing the beam from an axis of the beam; and (g) an alignment instrument mountable on a stage of the microscope system in the sample position and having a face plate with a spatially limited aperture therein which can be positioned at the focal point of the objective lens, the alignment instrument selectively activatable to provide light out through the aperture on the return beam path to the spectrograph and also selectively activatable to receive light through the aperture from the illumination light beam path and to detect the intensity of the light passed through the aperture.

8. The microscope system of claim 7, further including a computer controller connected to the alignment instrument to selectively activate the light source therein and to receive a signal from the alignment instrument detector related to the intensity of light detected by the detector, the computer controller connected to the spectrograph detector to receive a signal therefrom indicative of the intensity of the light detected by the spectrographic detector, the computer controller connected to the means for adjusting the illuminating beam path and the means for adjusting the return beam path to control the adjustment of the beam paths.

9. The microscope system of claim 7, wherein the means for adjusting the illumination beam path and the means for adjusting the return beam path each comprise a pair of sequential lenses, the lenses having focal lengths of equal magnitude but opposite sign to provide an optical system with negligible optical power through the pair of lenses, one of the lenses selectively displaceable in two dimensions with respect to the beam axis to carry out adjustment of the beam path.

10. The microscope system of claim 7, further including a deflecting mirror mounted for selective insertion into and out of the microscope visible light beam path, the deflecting mirror insertable into the microscope beam path to deflect the illumination beam from the source to the objective lens and to deflect Raman scattered light collected by the objective lens onto a return beam path extending to the spectrograph detector.

11. The microscope system of claim 10, further including a reflecting notch filter mounted in position to receive light on the illuminating beam path from the source and to reflect light at the wavelength of the illuminating beam toward the deflecting mirror, the notch filter formed to transmit light therethrough on the return beam path that is at the wavelengths of Raman scattered radiation.

12. The microscope system of claim 7, further including a video camera mounted to receive light on the microscope beam path from the sample position that is passed through the objective lens to form a video image of a sample.

13. The microscope system of claim 7, wherein the alignment instrument includes a housing, the face plate with the aperture therein forming part of the housing, wherein the light source and the light detector of the alignment instrument are mounted within the housing.

14. The microscope system of claim 13, wherein the alignment instrument further includes a casing for the light source mounted in the housing with the aperture opening into an interior of the casing through a lens, wherein the light source is mounted to the casing to project light through the lens and thence out the aperture when activated, and wherein the light detector is mounted to the casing to receive light that enters through the aperture into the casing interior.

* * * * *

UNITED STATES PATENT AND TRADEMARK OFFICE
CERTIFICATE OF CORRECTION

PATENT NO. : 6,661,509 B2 Page 1 of 1
DATED : December 9, 2003
INVENTOR(S) : Deck et al.

It is certified that error appears in the above-identified patent and that said Letters Patent is hereby corrected as shown below:

Column 4,
Line 54, delete the phrase "passes through a beam, path" and replace it with -- passes through a beam path --.

Column 9,
Line 5, delete "o#the" and replace it with -- of the --.

Signed and Sealed this

Tenth Day of August, 2004

JON W. DUDAS
*Acting Director of the United States Patent and Trademark Office*